(12) United States Patent
Stalker et al.

(10) Patent No.: US 6,443,979 B1
(45) Date of Patent: Sep. 3, 2002

(54) EXPANDABLE STENT DELIVERY SHEATH AND METHOD OF USE

(75) Inventors: Kent C. B. Stalker, San Marcos; Larry Voss, San Jose, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/469,150

(22) Filed: Dec. 20, 1999

(51) Int. Cl.[7] .................................................. A61F 2/06
(52) U.S. Cl. ...................................................... 623/1.11
(58) Field of Search ............................... 623/1.11, 1.12, 623/1.13–1.16; 606/194, 108, 195, 192, 123

(56) References Cited

U.S. PATENT DOCUMENTS

| | | |
|---|---|---|
| 3,868,956 A | 3/1975 | Alfidi et al. |
| 4,300,244 A | 11/1981 | Bokros |
| 4,323,071 A | 4/1982 | Simpson et al. |
| 4,332,254 A | 6/1982 | Lundquist |
| 4,439,185 A | 3/1984 | Lundquist |
| 4,468,224 A | 8/1984 | Enzmann et al. |
| 4,512,338 A | 4/1985 | Balko et al. |
| 4,516,972 A | 5/1985 | Samson |
| 4,538,622 A | 9/1985 | Samson et al. |
| 4,554,929 A | 11/1985 | Samson et al. |
| 4,569,347 A | 2/1986 | Frisbie |
| 4,571,240 A | 2/1986 | Samson et al. |
| 4,580,568 A | 4/1986 | Gianturco |
| 4,616,652 A | 10/1986 | Simpson |
| 4,655,771 A | 4/1987 | Wallsten |
| 4,733,665 A | 3/1988 | Palmaz |
| 4,738,666 A | * 4/1988 | Fuqua ........................ 604/280 |
| 4,739,762 A | 4/1988 | Palmaz |
| 4,740,207 A | 4/1988 | Kreamer |
| 4,748,982 A | 6/1988 | Horzewski et al. |
| 4,762,128 A | 8/1988 | Rosenbluth |
| 4,790,315 A | 12/1988 | Mueller, Jr. et al. |
| 4,795,458 A | 1/1989 | Regan |
| 4,800,882 A | 1/1989 | Gianturco |
| 4,830,003 A | 5/1989 | Wolff et al. |
| 4,878,906 A | 11/1989 | Lindemann et al. |
| 4,886,062 A | 12/1989 | Wiktor |
| 4,893,623 A | 1/1990 | Rosenbluth |
| 4,907,336 A | 3/1990 | Gianturco |
| 4,913,141 A | 4/1990 | Hillstead |

(List continued on next page.)

FOREIGN PATENT DOCUMENTS

| | | |
|---|---|---|
| EP | 0 556 940 A1 | 8/1993 |
| WO | WO 95/33422 | 12/1995 |
| WO | WO 96/39998 | 12/1996 |
| WO | WO 98/22159 | 5/1998 |
| WO | WO 98/53759 | 12/1998 |

OTHER PUBLICATIONS

Michael J. Wallace, et al.; "Tracheobronchial Tree: Expandable Metallic Stents Used in Experimental and Clinical Applications", Radiology, Feb., 1986, pp. 309–312.

"Coronary Wallstent Endoprosthesis", Schneider Innovation for Life, Schneider (Europe), Switzerland, 1986, 4 pages.

Primary Examiner—Henry J. Recla
Assistant Examiner—Tan-Uyen T. Ho
(74) Attorney, Agent, or Firm—Fulwider Patton Lee & Utecht, LLP

(57) ABSTRACT

An expandable delivery sheath is provided for intravascular introduction into a patient's vasculature by means of a guiding catheter. An interventional device, such as a stent delivery catheter, is subsequently advanced within the expandable sheath to a point where the stent traverses an arterial lesion. The sheath forms a protective barrier between the lesion and the stent and it delivery catheter, thereby preventing the creation of emboli which might otherwise be produced by abrasion of the stent against the plaque of the arterial lesion. Prior to expansion of the stent, the expandable sheath is retracted from the area of treatment.

29 Claims, 3 Drawing Sheets

U.S. PATENT DOCUMENTS

| | | | |
|---|---|---|---|
| B14,323,071 A | 5/1990 | Simpson et al. | |
| 4,950,227 A | 8/1990 | Savin et al. | |
| 4,969,458 A | 11/1990 | Wiktor | |
| 4,969,890 A | 11/1990 | Sugita et al. | |
| 4,990,115 A | 2/1991 | Wilkoff | |
| 4,998,539 A | 3/1991 | Delsanti | |
| 5,002,560 A | 3/1991 | Machold et al. | |
| 5,026,377 A | 6/1991 | Burton et al. | |
| 5,034,001 A | 7/1991 | Garrison et al. | |
| 5,035,706 A | 7/1991 | Giantureo et al. | |
| 5,037,392 A | 8/1991 | Hillstead | |
| 5,037,427 A | 8/1991 | Harada et al. | |
| 5,041,126 A | 8/1991 | Gianturco | |
| 5,059,166 A | 10/1991 | Fischell et al. | |
| 5,061,275 A | 10/1991 | Wallsten et al. | |
| 5,064,435 A | 11/1991 | Porter | |
| 5,071,407 A | 12/1991 | Termin et al. | |
| 5,078,720 A | 1/1992 | Burton et al. | |
| 5,089,005 A | 2/1992 | Harada | |
| 5,089,006 A | 2/1992 | Stiles | |
| 5,092,838 A * | 3/1992 | Kipperman | 604/53 |
| 5,092,877 A | 3/1992 | Pinchuk | |
| 5,102,417 A | 4/1992 | Palmaz | |
| 5,108,416 A | 4/1992 | Ryan et al. | |
| 5,123,917 A | 6/1992 | Lee | |
| 5,133,732 A | 7/1992 | Wiktor | |
| 5,135,517 A | 8/1992 | McCoy | |
| 5,137,513 A | 8/1992 | McInnes et al. | |
| 5,158,548 A | 10/1992 | Lau et al. | |
| 5,163,952 A | 11/1992 | Froix | |
| 5,163,958 A | 11/1992 | Pinchuk | |
| 5,171,262 A | 12/1992 | MacGregor | |
| 5,183,085 A | 2/1993 | Timmermans | |
| 5,192,297 A | 3/1993 | Hull | |
| 5,197,978 A | 3/1993 | Hess | |
| 5,222,964 A | 6/1993 | Cooper | |
| 5,222,969 A | 6/1993 | Gillis | |
| 5,222,971 A | 6/1993 | Willard et al. | |
| 5,226,913 A | 7/1993 | Pinchuk | |
| 5,242,451 A | 9/1993 | Harada et al. | |
| 5,250,070 A * | 10/1993 | Parodi | 606/194 |
| 5,256,146 A | 10/1993 | Ensminger et al. | |
| 5,258,020 A | 11/1993 | Froix | |
| 5,263,964 A | 11/1993 | Purdy | |
| B14,733,665 A | 1/1994 | Palmaz | |
| 5,282,823 A | 2/1994 | Schwartz et al. | |
| 5,285,824 A | 2/1994 | Gianturco | |
| 5,300,085 A | 4/1994 | Yock | |
| 5,304,200 A | 4/1994 | Spaulding | |
| 5,306,294 A | 4/1994 | Winston et al. | |
| 5,330,500 A | 7/1994 | Song | |
| 5,354,308 A | 10/1994 | Simon et al. | |
| 5,354,309 A | 10/1994 | Schnepp-Pesch et al. | |
| 5,356,423 A | 10/1994 | Tihon et al. | |
| 5,372,600 A | 12/1994 | Beyar et al. | |
| 5,378,239 A | 1/1995 | Termin et al. | |
| 5,391,172 A | 2/1995 | Williams et al. | |
| 5,395,390 A | 3/1995 | Simon et al. | |
| 5,403,341 A | 4/1995 | Solar | |
| 5,405,377 A | 4/1995 | Cragg | |
| 5,411,507 A | 5/1995 | Heckele | |
| 5,415,664 A | 5/1995 | Pinchuk | |
| 5,421,955 A | 6/1995 | Lau et al. | |
| 5,443,496 A | 8/1995 | Schwartz et al. | |
| 5,447,503 A | 9/1995 | Miller | |
| 5,449,373 A | 9/1995 | Pinchasik et al. | |
| 5,453,090 A * | 9/1995 | Martinez et al. | 623/1.11 |
| 5,456,694 A | 10/1995 | Marin et al. | |
| 5,458,615 A | 10/1995 | Klemm et al. | |
| 5,478,349 A | 12/1995 | Nicholas | |
| 5,484,444 A | 1/1996 | Braunschweiler et al. | |
| 5,496,277 A | 3/1996 | Termin et al. | |
| 5,496,346 A | 3/1996 | Horzewski et al. | |
| 5,507,767 A | 4/1996 | Maeda et al. | |
| 5,514,154 A | 5/1996 | Lau et al. | |
| 5,522,883 A | 6/1996 | Slater et al. | |
| 5,534,007 A | 7/1996 | St. Germain et al. | |
| 5,549,551 A * | 8/1996 | Peacock, III et al. | 606/194 |
| 5,554,181 A | 9/1996 | Das | |
| 5,569,295 A | 10/1996 | Lam | |
| 5,571,135 A | 11/1996 | Fraser et al. | |
| 5,571,168 A | 11/1996 | Toro | |
| 5,603,721 A | 2/1997 | Lau et al. | |
| 5,626,600 A | 5/1997 | Horzewski et al. | |
| 5,634,928 A | 6/1997 | Fischell et al. | |
| 5,653,727 A | 8/1997 | Wiktor | |
| B15,421,955 A | 1/1998 | Lau et al. | |
| 5,728,158 A | 3/1998 | Lau et al. | |
| 5,755,777 A | 5/1998 | Chuter | |
| 5,759,192 A | 6/1998 | Saunders | |
| 5,788,707 A | 8/1998 | Del Toro et al. | |
| 5,827,321 A | 10/1998 | Roubin et al. | |
| 5,836,965 A | 11/1998 | Jendersee et al. | |
| 5,843,117 A | 12/1998 | Alt et al. | |
| 5,871,537 A * | 2/1999 | Holman et al. | 623/1.11 |
| 5,888,201 A | 3/1999 | Stinson et al. | |
| 5,910,145 A | 6/1999 | Fischell et al. | |
| 5,925,061 A | 7/1999 | Ogi et al. | |
| 5,931,867 A | 8/1999 | Haindl | |
| 5,944,726 A | 8/1999 | Blaeser et al. | |
| 5,954,764 A | 9/1999 | Parodi | |
| 5,968,069 A | 10/1999 | Dusbabek et al. | |
| 5,980,533 A | 11/1999 | Holman | |
| 5,989,280 A | 11/1999 | Euteneuer et al. | |
| 6,001,123 A | 12/1999 | Lau | |
| 6,019,778 A | 2/2000 | Wilson et al. | |

\* cited by examiner

EXPANDABLE STENT DELIVERY SHEATH AND METHOD OF USE

BACKGROUND OF THE INVENTION

The present invention is directed to the field of percutaneous transluminal angioplasty (PTA) and percutaneous transluminal coronary angioplasty (PTCA) procedures generally, and more particularly, to a device and method which allow an interventional medical device, such as a stent-delivery catheter, to traverse an arterial lesion without dislodging friable arterial plaque during delivery of the interventional device through the lesion.

In a typical balloon angioplasty procedure, a guiding catheter is percutaneously introduced into the cardiovascular system of a patient through the femoral arteries by means of a conventional Seldinger technique and advanced within a patient's vascular system until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the lesion. Once in position, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter may be withdrawn from the patient's vasculature and the blood flow resumed through the dilated artery. As should be appreciated by those skilled in the art, while the above-described procedure is typical, it is not the only method used in angioplasty.

Angioplasty procedures, by necessity, stretch and tear the tissue of the artery wall in the region of treatment with a resultant reduction in strength. As a consequence, radial collapse of the vessel lumen occurs in a certain percentage of cases. In order to prevent radial collapse of a dilated vessel, a physician can implant an intravascular prosthesis for maintaining vascular patency across the dilated region. Such prostheses are small tubular metallic structures commonly referred to as stents. The stent is crimped tightly onto the balloon portion of a dilatation catheter and is advanced through the guiding catheter already in place in the patient's vasculature. The stent is positioned so that it bridges the dilated region when expanded by an expandable member, such as balloon, and is thus implanted in the artery.

In lightly occluded arteries, some physicians prefer to expand the artery and implant a stent in a single operation. However, in heavily occluded arteries, this procedure has proven somewhat dangerous as the metallic structure of the stent tends to dislodge the arterial plaque thereby forming emboli which will be released into the patient's bloodstream. Such emboli may become lodged in a small diameter blood vessel and can occlude or partially occlude the vessel. When angioplasty is performed in the carotid arteries, the risks associated with emboli are particularly high since emboli which may be produced present a significant risk of ischemic stroke should a blood vessel leading to the brain become occluded.

Therefore, in heavily occluded vessels, the presently preferred procedure is to first dilate the artery across the lesion site and withdraw the dilatation catheter. This step is commonly referred to as pre-dilatation. In a second step, a stent is expanded and implanted across the previously dilated lesion site usually by means of a second delivery catheter. This two-step procedure is advantageous since the stent is less likely to dislodge arterial plaque in the pre-dilated artery and therefore the risk posed by emboli is somewhat reduced. However, the two-step procedure has some disadvantages in that the artery wall undergoes additional trauma during the second dilatation procedure and may suffer additional loss of strength.

The majority of devices that have been proposed as solutions to the problem of emboli generated during an angioplasty procedure may be categorized as intravascular filters that attempt to capture or trap emboli flowing within the patient's blood stream. There are many examples of such filters, one of which is described in U.S. Pat. No. 5,152,777, entitled "Device and Method for Providing Protection From Emboli and Preventing Occlusion of Blood Vessels" issued to Goldberg et al. This device consists of a filter having of a plurality of resilient, stainless steel wire arms joined at one end so as to form a conical surface, and having rounded tips at their other ends to prevent damage to the vessel walls. This filter is intended to be removable and is designed to be deployed from either a small diameter catheter or a hollow guidewire.

Another example of an intravascular filter is described in U.S. Pat. No. 4,873,978, entitled "Device and Method for Emboli Retrieval" issued to Ginsburg. Ginsburg discloses a removable vascular filter permanently attached to a wire for deployment from a catheter. The filter is comprised of a bundle of longitudinal wires secured together at the point of attachment to the deployment wire. Interconnecting each adjacent longitudinal wire is a transverse wire which forms a zig-zag pattern. The filter is introduced through a catheter. Upon deployment, the filter wires expand to form a wire mesh, thereby obstructing the vessel and straining the blood flowing there through.

One drawback of many prior art filtering devices is the relatively large size of the wire mesh or straining elements used in the filters. Large mesh filters may allow for adequate blood flow but sometimes fail to trap all of the small emboli. Fine mesh filters may not provide an adequate solution to this problem as they generally have a low percolation rate which may tend to limit blood flow within the vessel and may induce blood depravation downstream from the area of deployment. In addition, the various prior art devices do nothing to alleviate the need for pre-dilatation of heavily occluded arteries prior to stent placement.

Given these and other limitations of the prior art filters, it becomes apparent that there is a need for an alternative device or method that would reduce the likelihood of emboli formation during an interventional procedure and would therefore increase the efficacy of existing intravascular filters. Ideally, such a device would also allow a stent delivery catheter to be introduced into a highly occluded artery without the necessity of pre-dilatation and would therefore reduce trauma imposed on an artery wall. Further, such a device should be compatible with existing catheters and other equipment used in angioplasty procedures. The present invention satisfies these and other needs.

SUMMARY OF THE INVENTION

The present invention provides an elastically and/or geometrically expandable, low friction, low profile delivery sheath attached to the distal end of a catheter. The delivery sheath serves to form a protective barrier between arterial lesions composed of friable arterial plaque and an interventional device, such as a stent delivery catheter, subsequently introduced through the sheath to treat the lesion. In use, the expandable delivery sheath is introduced into a guiding catheter which has been previously placed at a location proximal to the lesion site. The expandable sheath is advanced through the guiding catheter and deployed such that it traverses the arterial lesion. Due to its low profile and elastic nature, the delivery sheath should not dislodge arterial plaque in a highly occluded artery. A stent delivery catheter then can be introduced into the expandable sheath. The expandable sheath, which is designed to have a diameter smaller than that of the stent delivery catheter, expands upon introduction of the stent delivery catheter to form a glove-like fit over the stent and its delivery catheter. Due to the sheath's low coefficient of friction, the stent delivery catheter may be easily advanced through the sheath until the stent bridges the lesion within an artery. As the stent and its delivery catheter traverse the lesion, the sheath forms a protective barrier between the stent and the friable arterial plaque of the lesion to help prevent the formation of emboli that would otherwise be created by abrasive forces if the stent crossed the lesion without the presence of such a delivery sheath.

The delivery of the stent delivery catheter also causes the lesion to compress somewhat to conform to the larger diameter of the stent delivery catheter. In this manner, the advancement of the stent delivery catheter across the lesion provides some pre-dilatation of the stenosis. Prior to expansion of the stent, the delivery sheath, having served its purpose, can be withdrawn from the area of treatment back into the guiding catheter. Thereafter, the stent can be expanded fully in the artery to compress the lesion and restore adequate blood flow through the area of treatment.

The present invention reduces the likelihood of emboli formation by providing a low profile sheath that may easily cross a lesion without abrading the lesion. Once in place, the delivery sheath forms a protective barrier between the lesion and any subsequently introduced interventional device. Thus, the expandable sheath of the present invention increases the safety and efficacy when performing interventional procedures. In addition, the present invention may reduce the need for pre-dilatation of a lesion prior to placement of the stent to thereby minimize trauma to the artery wall.

These and other advantages of the invention will become more apparent from the following detailed description of the invention when taken in conjunction with the accompanying exemplary drawings.

DETAILED DESCRIPTION OF THE PREFERRED EMBODIMENTS

Figure 1:
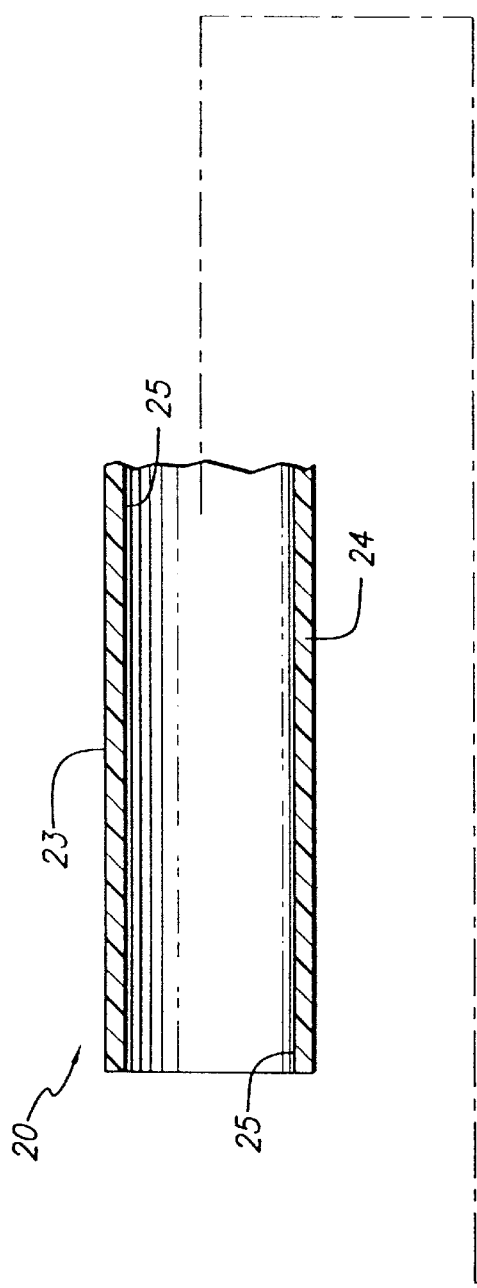
FIG. 1 depicts a side elevational view, partially in cross-section, of an expandable delivery sheath device according to the present invention as it is inserted into a body vessel, partially extending from a guiding catheter at an atherosclerotic plaque site.
Figure 1:
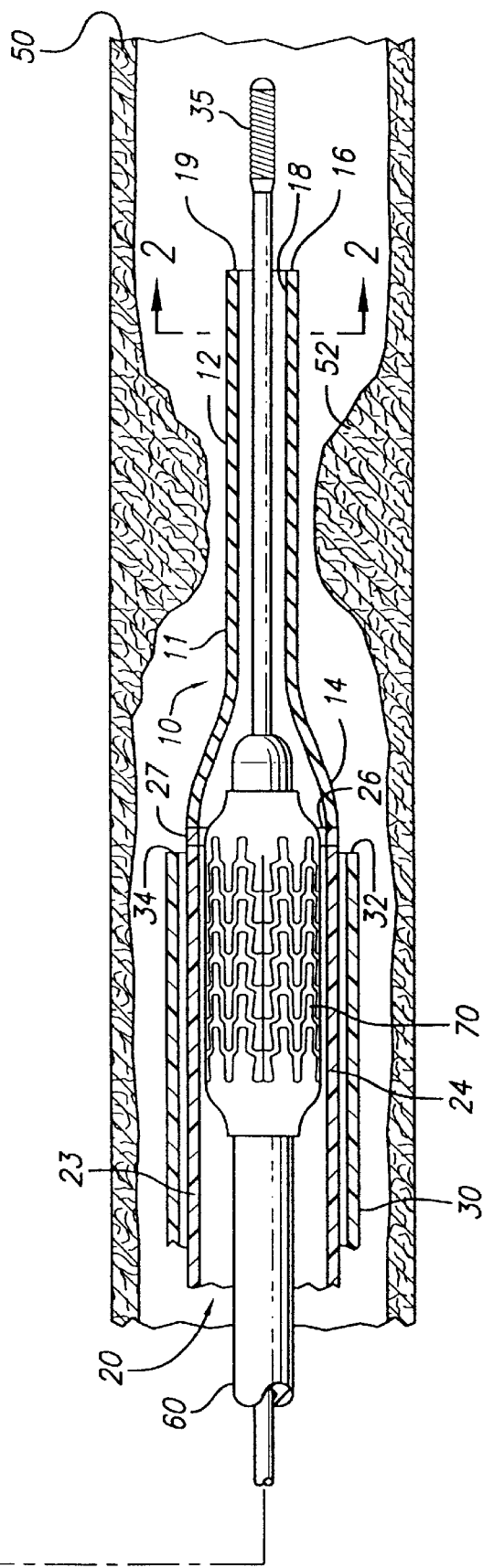

With reference to FIG. 1, one preferred embodiment of the expandable delivery sheath device 10 of the present invention is shown. The expandable delivery sheath device 10 is comprised generally of an expandable distal sheath portion 11 and a deployment catheter 20. The expandable distal sheath portion 11 includes a tubular wall 12 with a proximal end 14 and a distal end 16, defining an inner lumen 18 which extends there between. The expandable sheath 10, as depicted in FIG. 1, is shown in its non-expanded configuration.

Figure 2A:
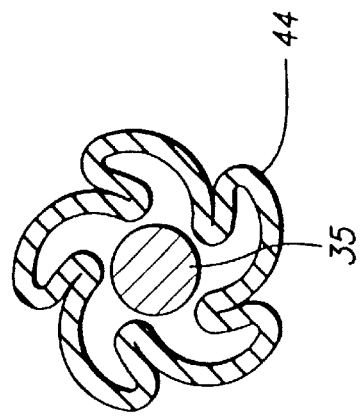
FIG. 2a is a sectional view of the expandable delivery sheath device taken along line 2—2 of FIG. 1.
Figure 2B:
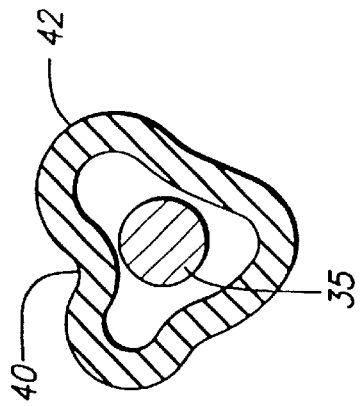
FIG. 2b is a cross-sectional view, similar to FIG. 2a, of an alternative embodiment of the expandable delivery sheath device.

To be operable, the distal expandable sheath portion 11 must be able to expand from an initial, low profile diameter to a second larger diameter which corresponds to the diameter of the interventional device, such as a stent-delivery catheter. Sheath expansion may be accomplished through material elasticity alone or through a combination of material elasticity and geometric expansion. As used here, expansion due to material elasticity refers to radially outward expansion of the sheath due to the force exerted in advancing a catheter or other intravascular device through distal sheath portion 11, whereas geometric expansion refers to expansion accomplished by utilizing an inwardly foldable configuration, for achieving a low profile, which allows the expandable distal sheath portion 11 to unfold to a larger diameter upon insertion of an intravascular device. In geometric expansion, a minimal amount of force is usually required to cause the foldable cross-section to expand. FIG. 2a depicts an embodiment where the expansion ratio of distal sheath portion 11 is primarily a function of material elasticity. Distal sheath portion 11 has an annular cross-section with an inner lumen 18. FIG. 2b depicts an alternative embodiment where the expansion ratio of distal sheath portion 11 is a function of material elasticity and of the geometric configuration of the sheath. In FIG. 2b, the cross-section of the distal sheath portion is composed of a plurality of equally spaced foldable sectors 40 of a convex radius. Each adjacent sector 40 is blended into the next sector by a concave radii 42.

Figure 2C:
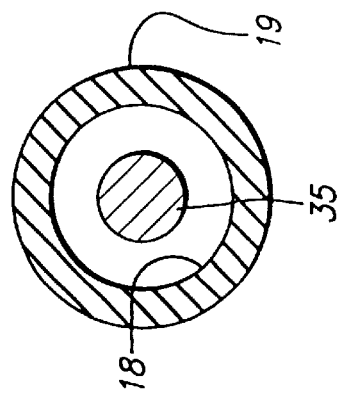
FIG. 2c is a cross-sectional view, similar to FIG. 2a, of another embodiment of an expandable delivery sheath device.

FIG. 2c depicts another embodiment of the expandable distal sheath portion 11 where the expansion ratio is a function of both material elasticity and geometric configuration. Here, the cross-section of distal sheath portion 11 is in the form of a plurality of equally spaced and interconnected foldable spiral arms 44. FIGS. 2a, 2b, and 2c are not intended to be inclusive of all sheath designs, as other similar foldable cross-sections also can be used in accordance with the present invention.

Distal sheath portion 11 can be formed from an elastomeric material possessing a low modulus of elasticity and a low coefficient of friction. Although, some plastic deformation is acceptable, it is preferable that the material chosen be capable of linear elastic expansion from the sheath's initial delivery diameter to the expanded diameter when the selected stent carrying-catheter or other lesion treatment device is placed into the inner lumen 18 of the distal sheath portion 11. Examples of suitable materials are the polyolefinic ionomers of the sodium, lithium and zinc types.

These ionomers are commercially available from the E.I. Dupont de Nemours Corporation under the trademark SURLYN. Polyolefinic ionomers which have been irradiated to cross link the polymers are also suitable as are blends of polyolefin and polyethylene. Other bio-compatible polymeric materials, blends of materials, and cross-linked materials, which exhibit elastomeric properties may also be suitable. When the distal sheath portion 11 is made from a polyolefin material, an expansion ratio of 1.75:1 is readily obtainable with the annular cross-section depicted in FIG. 2a. Expansion ratios exceeding 4:1 may be achieved where elastic materials are used to form geometrically expandable cross-sections such as those shown in FIGS. 2b and 2c. In the preferred embodiment, the distal sheath portion 11 utilizes a combination of material elasticity and foldable geometric cross-sections to achieve a high expansion ratio. However, embodiments of the distal sheath portion 11 which depend solely on geometric expansion are practicable. Embodiments of this type may be readily produced by manufacturing sheaths with the cross-sections depicted in FIGS. 2b and 2c from relatively inelastic, biologically inert materials such as polyethylene and polypropylene. Distal sheath portion 11 may be formed as a continuous length of tubing by any known extrusion, drawing, molding, or similar production process.

Catheter 20, comprises an elongated tubular member 23 with a wall thickness 24, having a proximal end 25 and a distal end 27. Catheter 20 is sufficiently rigid such that it may be easily advanced through a guiding catheter without risk of buckling. Catheter 20 can be manufactured from polyethylene, polypropylene, or other suitable biocompatible material, utilizing any known manufacturing process such as extrusion or drawing. The distal end 27 of catheter 20 is attached to the proximal end of expandable distal sheath portion 11 by conventional means such as heat welding, solvent welding, ultrasonic welding, adhesive bonding or any other suitable method. After fabrication, selected lengths of the expandable sheath device may be packaged in sealed inert polyethylene bags and then sterilized by irradiation techniques well known to those skilled in the art.

Referring now again to FIG. 1, a preferred method of use of the sheath device of the present invention is as follows. A guiding catheter 30 is percutaneously introduced into a patient's vasculature, using a conventional Seldinger technique, and is advanced through the patient's body lumen 50 until its distal end 32 lies proximal to an arterial lesion 52. Preferably, guiding catheter 30 is equipped with a radiopaque marker 34 on its distal end 32. The physician may accurately place guiding catheter 30 within body lumen 50 by tracking the progress of radiopaque marker 34 on an x-ray, fluoroscope, or similar visualization equipment. Subsequently, a guidewire 35 is advanced through the guiding catheter until its distal end lies distal of the arterial lesion. After placement of the guidewire, expandable sheath device 10 is advanced over the guidewire and through catheter 30 until the distal end 16 of distal sheath portion 11 is advanced out of catheter 30 to a point distal to the lesion 50. The sheath device 10 may also be equipped with a radiopaque marker 19 to aid the physician in placing the sheath device. Once the distal sheath portion 11 has traversed lesion 50, it should be suitably positioned to protect lesion 50 from abrasion by any subsequently introduced stent-bearing catheter or other intravascular device.

Figure 3:
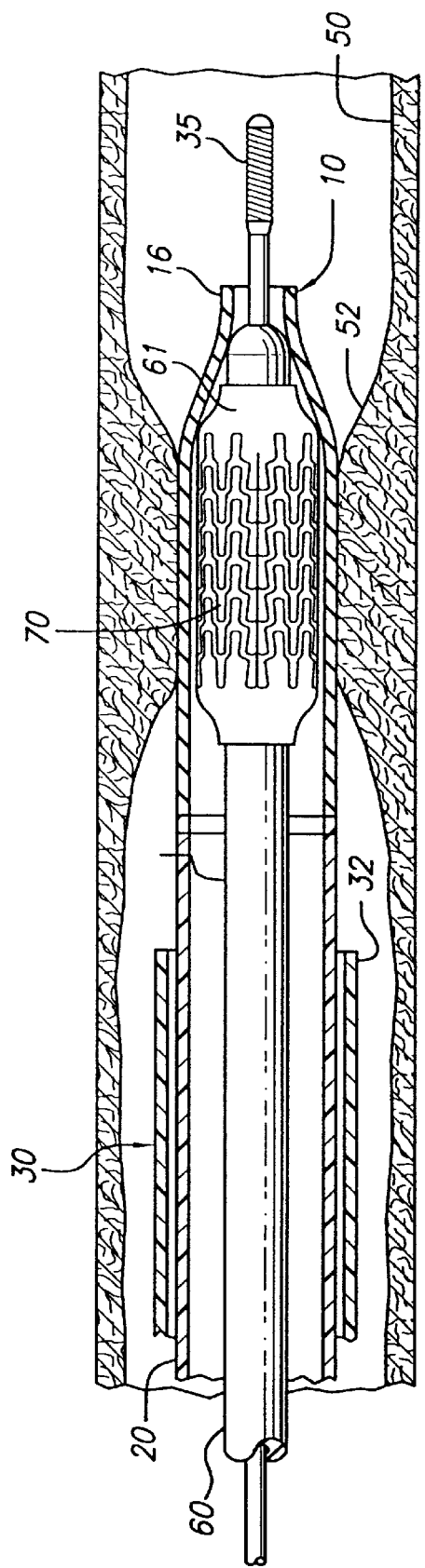
FIG. 3 depicts a side view, partially in cross-section, of the expandable delivery sheath device of FIG. 1, with a stent delivery catheter advanced within the expandable distal sheath portion at the atherosclerotic plaque site.

Referring now to FIG. 3, a stent delivery catheter 60 with a stent 70 crimped to the dilatation balloon 61 is advanced through catheter 20 of expandable sheath device 10, and is further advanced through distal sheath portion 11, until the stent 70 traverses the arterial lesion 52. Advancement of stent-delivery catheter 60 into distal sheath portion 11 causes distal sheath portion 11 to expand and closely conform to the exterior profile of the stent-delivery catheter. Thereby distal sheath portion 11 forms a barrier to protect the lesion 52 from abrasion which would otherwise be caused by the stent 70 and also minimizing the formation of emboli.

Figure 4:
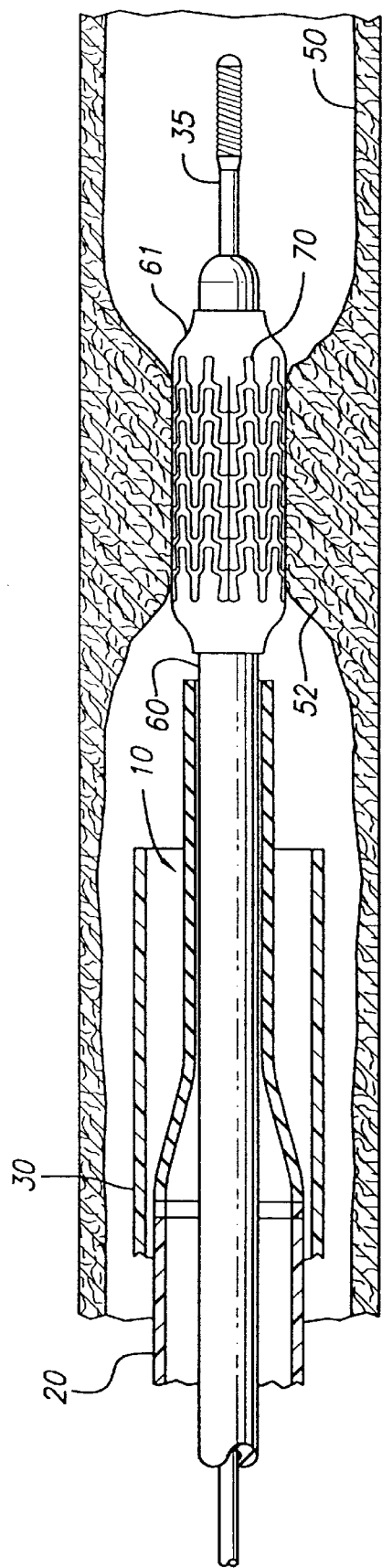
FIG. 4 depicts a side view, partially in cross-section, of the expandable delivery sheath device of FIG. 1, with the stent delivery catheter advanced beyond the distal sheath portion into the atherosclerotic plaque site.

Referring now to FIG. 4, sheath device 10 is retracted into guiding catheter 30, by adjusting the position of deployment catheter 20 relative to guiding catheter 30, thereby exposing stent-delivery catheter 60 and stent 70. At this point in the procedure, stent 70 is expanded and implanted into vessel lumen 50, across lesion 52, in accordance with typical angioplasty practice; namely dilatation balloon 61 is expanded by means of a radiopaque liquid delivered at high pressure, which forces the stent to radially expand against the lumen wall, thereby dilating the lumen and firmly implanting the stent into the vessel wall.

The stent employed with the device of the present invention should ideally have an expanded configuration that will trap relatively small particles of plaque, and should thus have a relatively small spacing between the wires, struts, or other elements that form the stent. Co-owned U.S. Pat. No. 5,514,154 to Lau et al., U.S. Pat. No. 5,569,295 to Lam, U.S. Pat. No. 5,591,197 to Orth et al., U.S. Pat. No. 5,603,721 to Lau et al., U.S. Pat. No. 5,649,952 to Lam, U.S. Pat. No. 5,728,158 to Lau et al., and U.S. Pat. No. 5,735,893 to Lau et al. describe suitable stents, and these patents are hereby incorporated herein in their entirety by reference thereto. The above list is exemplary and is not inclusive. Other stent designs are also suitable and the stent could be a self-expanding stent made from NiTi alloys or other self-expanding or shape memory materials.

The method of use described above is exemplary and is not intended to be limiting. The expandable delivery sheath 10 may be used without the aid of the guiding catheter 30. Additionally, the catheter body 20 of the delivery sheath 10 may be used in place of the guiding catheter 30.

In view of the foregoing, it is apparent that the device and method of the present invention substantially enhances the safety of angioplasty procedures by significantly reducing the risk associated with frangible plaque deposits breaking away from the vascular wall and migrating into the patient's blood stream in the form of emboli, where such emboli may cause serious harm to the patient in form of stroke. In addition, in a significant number of cases the device and method of the present invention will allow for the dilatation and placement of a stent in a heavily occluded artery to be performed in a single operation, thereby eliminating the need for pre-dilatating such arteries. By eliminating the pre-dilatation step, a diseased artery is spared additional trauma and may suffer less degradation in strength. Further, by dilating the artery and placing the stent in a single operation, the possibility of radial collapse of the vessel can be substantially reduced.

It will be appreciated that a novel device and method for preventing the formation of emboli during an angioplasty procedure has been presented. While only the presently preferred embodiments have been described in detail, as will be apparent to those skilled in the art, modifications and improvements may be made to the device and method disclosed herein without departing from the scope of the invention. Accordingly, it is not intended that the invention be limited, except as by the appended claims.

What is claimed:

1. A delivery sheath device for use with an interventional device which protects a lesion from abrasion caused by the delivery of the interventional device through the lesion, comprising:

an expandable sheath portion having a proximal end and a distal end, with an inner lumen extending therethrough, the sheath portion having a substantial constant low profile diameter to cross the lesion and being expandable against the lesion by the subsequent introduction of an interventional device into the inner lumen to prevent abrasion between the interventional device and the lesion; and a catheter portion having a proximal end and a distal end, with an inner lumen extending therethrough, wherein the distal end of the catheter portion is attached to proximal end of the expandable sheath portion and the inner lumen of the catheter portion is used to deliver the interventional device into the inner lumen of the expandable sheath portion, the inner lumen of the catheter portion being larger than the inner lumen of the expandable sheath portion prior to the introduction of the interventional device into the inner lumen of the expandable sheath.

2. The device of claim 1, wherein the expandable sheath portion is elastically expandable.

3. The device of claim 1, wherein the expandable sheath portion is geometrically expandable.

4. The device of claim 1, wherein the expandable sheath portion is elastically and geometrically expandable.

5. The device of claim 1, wherein the expandable sheath portion is of annular cross-section.

6. The device of claim 1, wherein a radiopaque marker is attached to the distal end of the sheath portion.

7. The device of claim 1, wherein the expandable sheath portion is made from an elastomeric material.

8. The device of claim 1, wherein the expandable sheath portion has a foldable cross-section.

9. The device of claim 8, wherein said foldable cross-section includes a plurality of equally spaced radially convex sectors.

10. The device of claim 8, wherein said foldable cross-section includes a plurality of equally spaced spiral arms.

11. The device of claim 1, wherein:

the expandable sheath portion and catheter portion are made from different materials.

12. The device of claim 11, wherein:

the expandable sheath portion is made from a material having greater expandability than the material used for the catheter portion.

13. The device of claim 1, wherein:

the expandable sheath portion has a length at least as long as the length of the lesion to be treated.

14. The device of claim 1, wherein:

the expandable sheath portion is as long as the interventional device used with the delivery sheath device.

15. The device of claim 1, wherein:

the inner lumen of the catheter portion is used to maintain the interventional device in an initial delivery position, the interventional device being positioned near the distal end of the catheter portion while in the initial delivery position, the interventional device being moveable into the expandable sheath portion after the expandable sheath portion crosses the lesion.

16. The device of claim 15, wherein:

the inner lumen of the catheter portion has a diameter which permits the interventional device to extend therethrough without causing expansion of the catheter portion.

17. The device of claim 1, wherein:

the expandable sheath portion is resiliently expandable.

18. A method for providing a protective barrier between a lesion and an intravascular device advanced to the lesion site for treatment of the lesion, comprising the steps of:

percutaneously introducing a guiding catheter and advancing the guiding catheter to a point proximal to the lesion;

providing a radially outwardly expandable sheath having a proximal end and a distal end;

advancing the expandable sheath through the guiding catheter to a point distal of the lesion, whereby the expandable sheath fully traverses the lesion and thereby protects the lesion from abrasion;

providing an intravascular device for treatment of the lesion;

advancing the intravascular device through the expandable sheath until the treatment device is properly positioned for treatment of the lesion, the advancement of the intravascular device within the expandable sheath causing the sheath to expand;

retracting the expandable sheath thereby exposing the intravascular device; and operating the intravascular device to treat the lesion.

19. The method of claim 18, wherein the expandable sheath is an elastically expandable sheath.

20. The method of claim 18, wherein the expandable sheath is a geometrically expandable sheath.

21. The method of claim 18, wherein the expandable sheath is an elastically and geometrically expandable sheath.

22. The method of claim 18, wherein the intravascular treatment device is a balloon dilatation catheter.

23. The method of claim 18, wherein the intravascular treatment device is a stent and stent-delivery catheter.

24. A method for providing a protective barrier between a lesion and an intervascular device advanced to the lesion site for treatment of the lesion, comprising:

providing an expandable sheath portion having an inner lumen extending therethrough and a catheter portion attached to the expandable sheath portion which includes an inner lumen extending therethrough, the inner lumen of the catheter portion being used to deliver the interventional device into the inner lumen of the expandable sheath portion;

providing an intravascular device for treatment of the lesion;

advancing the intravascular device through the catheter portion into a first delivery position;

advancing the expandable sheath portion across the lesion to provide a protective barrier which protects the lesion from abrasion of the intravascular device;

advancing the intravascular device through the expandable sheath portion causing the expandable sheath portion to expand radially towards the lesion, allowing the intravascular device to be positioned for treatment of the lesion;

retracting the sheath portion to expose the intravascular device; and operating the intravascular device to treat the lesion.

25. The method of claim 24, wherein the expandable sheath is an elastically expandable sheath.

26. The method of claim 24, wherein the expandable sheath is a geometrically expandable sheath.

27. The method of claim 24, wherein the expandable sheath is an elastically and geometrically expandable sheath.

28. The method of claim 24, wherein:

the intravascular device is a balloon dilatation catheter.

29. The method of claim 24, wherein:

the intravascular device is a stent mounted on a stent delivery catheter.

* * * * *

UNITED STATES PATENT AND TRADEMARK OFFICE
CERTIFICATE OF CORRECTION

PATENT NO.    : 6,443,979 B1
DATED         : September 3, 2002
INVENTOR(S)   : Kent C. B. Stalker et al.

It is certified that error appears in the above-identified patent and that said Letters Patent is hereby corrected as shown below:

<u>Title page,</u>
Item [56], U.S. PATENT DOCUMENTS, change "5,285,824", to read -- 5,282,824 --.

Signed and Sealed this

Thirty-first Day of December, 2002

JAMES E. ROGAN
*Director of the United States Patent and Trademark Office*